(12) United States Patent
Chen et al.

(10) Patent No.: US 11,873,484 B2
(45) Date of Patent: Jan. 16, 2024

(54) OLIGONUCLEOTIDE ASSEMBLY USING ELECTRICALLY CONTROLLED HYBRIDIZATION

(71) Applicant: MICROSOFT TECHNOLOGY LICENSING, LLC, Redmond, WA (US)

(72) Inventors: Yuan-Jyue Chen, Seattle, WA (US); Bichlien Nguyen, Seattle, WA (US); Jake Smith, Seattle, WA (US); Karin Strauss, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 895 days.

(21) Appl. No.: 16/698,860

(22) Filed: Nov. 27, 2019

(65) Prior Publication Data

US 2021/0155923 A1 May 27, 2021

(51) Int. Cl.
| | |
|---|---|
| *C12N 15/10* | (2006.01) |
| *B01L 3/00* | (2006.01) |
| *C12Q 1/6874* | (2018.01) |
| *G06N 3/123* | (2023.01) |
| *G11C 13/02* | (2006.01) |
| *G16B 50/40* | (2019.01) |

(52) U.S. Cl.
CPC .... *C12N 15/1093* (2013.01); *B01L 3/502761* (2013.01); *C12Q 1/6874* (2013.01); *G06N 3/123* (2013.01); *G11C 13/02* (2013.01); *G16B 50/40* (2019.02); *B01J 2219/00722* (2013.01); *B01L 2200/0647* (2013.01); *B01L 2300/06* (2013.01); *B01L 2300/0636* (2013.01); *B01L 2300/0645* (2013.01); *B01L 2300/16* (2013.01)

(58) Field of Classification Search
CPC ........... C12N 15/1093; B01L 3/502761; B01L 2200/0647; B01L 2300/06; B01L 2300/0636; B01L 2300/0645; B01L 2300/16; C12Q 1/6874; C12Q 1/6806; C12Q 1/6834; C12Q 2521/501; C12Q 2523/109; C12Q 2523/303; C12Q 2523/307; C12Q 2537/149; C12Q 2565/607; C12Q 2565/629; G06N 3/123; G11C 13/02; G16B 50/40; G16B 50/00; B01J 2219/00722
See application file for complete search history.

(56) References Cited

U.S. PATENT DOCUMENTS

| | | | |
|---|---|---|---|
| 6,043,353 A | 3/2000 | Pon et al. | |
| 2019/0275492 A1 | 9/2019 | Efcavitch et al. | |
| 2020/0199662 A1 | 6/2020 | Strauss et al. | |
| 2020/0256862 A1 | 8/2020 | Shalek et al. | |
| 2020/0384434 A1 | 12/2020 | Nguyen et al. | |
| 2021/0205775 A1 | 7/2021 | Nguyen et al. | |
| 2022/0389483 A1 | 12/2022 | Chen et al. | |

FOREIGN PATENT DOCUMENTS

| | | | |
|---|---|---|---|
| CN | 109830263 A | | 5/2019 |
| EP | 1557464 A1 | | 7/2005 |
| WO | WO 96/01836 | * | 1/1996 |
| WO | 9637630 A1 | | 11/1996 |
| WO | 9731256 A2 | | 8/1997 |
| WO | 0220541 A2 | | 3/2002 |
| WO | 02072791 A2 | | 9/2002 |
| WO | 2017223517 A1 | | 12/2017 |
| WO | 2018102064 A1 | | 6/2018 |
| WO | 2019084058 A2 | | 5/2019 |
| WO | 2019226314 A1 | | 11/2019 |

OTHER PUBLICATIONS

Edman et al., Electric field directed nucleic acid hybridization on microchips, 1997, Nucleic Acids Research, 25, 4907-4914 (Year: 1997).*

Ghindilis, et al., "CombiMatrix oligonucleotide arrays: Genotyping and Gene Expression assays Employing Electrochemical Detection", In Proceedings of Biosensors & Bioelectronics, vol. 22, Issue 9-10, Apr. 15, 2007, pp. 1853-1860.

Hughes, et al., "Synthetic DNA Synthesis and Assembly: Putting the Synthetic in Synthetic Biology", In Proceedings of Cold Spring Harbor Perspectives in Biology, vol. 9, Issue 1, Jan. 1, 2017, 18 Pages.

Lopez, et al., "DNA Assembly for Nanopore Data Storage Readout", In Journal of Nature Communication, vol. 10, Issue 1, Jul. 3, 2019, 9 Pages.

Maurer, et al., "Electrochemically Generated Acid and Its Containment to 100 Micron Reaction Areas for the Production of DNA Microarrays", In Journal of Plos One, vol. 1, Issue 1, Dec. 20, 2006, 7 Pages.

Takahashi, et al., "Demonstration of End-to-End Automation of DNA Data Storage", In Journal of Scientific Reports, vol. 09, Issue 1, Mar. 21, 2019, 5 Pages.

(Continued)

*Primary Examiner* — Narayan K Bhat
(74) *Attorney, Agent, or Firm* — Newport IP, LLC; Benjamin A. Keim

(57) ABSTRACT

Electrically controlled hybridization is used to selectively assemble oligonucleotides on the surface of a microelectrode array. Controlled activation of individual electrodes in the microelectrode array attracts oligonucleotides in solution to specific regions of the array where they hybridize to other oligonucleotides anchored on the array. The oligonucleotides that hybridize may provide locations for subsequent oligonucleotides to hybridize. The active electrodes and the oligonucleotides in solution may be varied during each round of synthesis. This allows for multiple oligonucleotides each with different and specific sequences to be created in parallel. This is accomplished without the use of phosphoramidite chemical synthesis or template-independent DNA polymerase enzymatic synthesis. Oligonucleotides created with these techniques may be used to encode digital data. Fully assembled oligonucleotides may be separated from the array and sequenced, stored, or otherwise processed.

20 Claims, 8 Drawing Sheets

(56) References Cited

OTHER PUBLICATIONS

"International Search Report and Written Opinion Issued in PCT Application No. PCT/US20/059761", dated Feb. 17, 2021, 15 Pages.

Organick, et al., "Random Access in Large-Scale DNA Data Storage", In Journal of Nature biotechnology, vol. 36, Issue 3, Mar. 1, 2018, pp. 242-248.

"International Search Report and Written Opinion Issued in PCT Application No. PCT/US22/028408", dated Aug. 12, 2022, 12 Pages.

West, Ryan M., "Review-Electrical Manipulation of DNA Self-Assembled Monolayers: Electrochemical Melting of Surface-Bound DNA", In Journal of The Electrochemical Society, vol. 167, Issue 3, Jan. 21, 2020, 9 Pages.

Bi, et al., "Building Addressable Libraries: The Use of "Safety-Catch" Linkers on Microelectrode Arrays", In Journal of the American Chemical Society, vol. 132, Issue 49, Nov. 19, 2010, pp. 17405-17407.

Egeland, et al., "Electrochemically Directed Synthesis of Oligonucleotides for DNA Microarray Fabrication", In Journal of Nucleic Acids Research, vol. 33, Issue 14, Aug. 5, 2005, 7 Pages.

El-Sagheer, et al., "Click Nucleic Acid Ligation: Applications in Biology and Nanotechnology", In Journal of Accounts of Chemical Research, vol. 45, Issue 8, Mar. 22, 2012, pp. 1258-1267.

Hoff, et al., "Rapid and Dynamic Nucleic Acid Hybridization Enables Enzymatic Oligonucleotide Synthesis by Cyclic Reversible Termination: A Novel Mechanism for Enzymatic DNA Synthesis", In Repository of bioRxiv, Apr. 15, 2019, 23 Pages.

Song, et al., "DNA Multi-bit Non-volatile Memory and Bit-shifting Operations using Addressable Electrode Arrays and Electric Field-induced Hybridization", In Journal of Nature Communications, vol. 9, Article No. 281, Jan. 18, 2018, 8 Pages.

Adam, et al., "Electrochemical Monitoring of the Reversible Folding of Surface-Immobilized DNA i-Motifs", In Journal of Langmuir, vol. 34, Issue 9, Feb. 26, 2018, pp. 3112-3118.

Ma, et al., "Single-Stranded DNA Cleavage by Divergent CRISPR-Cas9 Enzymes", In Journal of Molecular Cell, vol. 60, Issue 3, Nov. 5, 2015, pp. 398-407.

"International Search Report and Written Opinion Issued in PCT Application No. PCT/US20/067392", dated Apr. 21, 2021, 14 Pages.

"Restriction Endonuclease Bst XI", In Journal of Roche Applied Science, 2011, 2 Pages.

"Restriction Endonuclease Pst I", In Journal of Roche Applied Sciences, 2012, 2 Pages.

"Non Final Office Action Issued in U.S. Appl. No. 16/735,628", dated Sep. 26, 2022, 15 Pages.

"Final Office Action Issued in U.S. Appl. No. 16/735,628", dated Apr. 7, 2023, 24 Pages.

Motea, et al., "Terminal Deoxynucleotidyl Transferase: The Story of a Misguided DNA Polymerase", In Journal of Biochimica et Biophysica Acta (BBA)-Proteins and Proteomics, vol. 1804, Issue 5, May 1, 2010, pp. 1151-1166.

"Notice of Allowance Issued in European Patent Application No. 20817573.7", dated Jul. 18, 2023, 8 Pages.

2021-0205775-A1, filed Jul. 8, 2021 Sep. 17, 2023.

U.S. Appl. No. 17/338,012, filed Jun. 3, 2021, Sep. 17, 2023.

"Non Final Office Action Issued in U.S. Appl. No. 17/338,012", dated Jul. 26, 2023, 25 Pages.

Day, et al., "i-Motif DNA: Structure, Stability and Targeting with Ligands", In Journal of Bioorganic & Medicinal Chemistry, vol. 22, Issue 16, Aug. 15, 2014, pp. 4407-4418.

Gamella, et al., "DNA Computing Systems Activated by Electrochemically-triggered DNA Release from a Polymer-brush-modified Electrode Array", In Journal of Electroanalysis, vol. 29, Issue 2, Feb. 10, 2017, pp. 398-408.

Li, et al., "Development and Applications of the Copper-Catalyzed Azide-Alkyne Cycloaddition (CuAAC) as a Bioorthogonal Reaction", In Journal of Molecules, vol. 21, Issue 10, Oct. 24, 2016, 22 Pages.

Rahman, et al., "A Highly Sensitive Electrochemical DNA Biosensor from Acrylic-Gold Nanocomposite for the Determination of Arowana Fish Gender", In Nanoscale Research Letters, vol. 12, Aug. 10, 2017, 10 Pages.

Wong, et al., "Directed Hybridization and Melting of DNA Linkers using Counterion-Screened Electric Fields", In Journal of Nano Letters, vol. 9, Issue 10, Jul. 16, 2009, pp. 3521-3526.

"Non Final Office Action Issued in U.S. Appl. No. 16/735,628", dated Aug. 30, 2023, 32 Pages.

\* cited by examiner

OLIGONUCLEOTIDE ASSEMBLY USING ELECTRICALLY CONTROLLED HYBRIDIZATION

BACKGROUND

The vast majority of artificially synthesized oligonucleotides are created by chemical synthesis using the phosphoramidite process. This process involves multiple steps and is performed using the organic solvent acetonitrile. Oligonucleotides may also be synthesized with a template-independent DNA polymerase, terminal deoxynucleotidyl transferase (TdT). TdT is a protein that evolved to rapidly catalyze the linkage of naturally occurring dNTPs.

However, both techniques have drawbacks. The phosphoramidite process is complex and creates organic waste that can be hazardous and expensive to process. It is also difficult to create oligonucleotides longer than 200-300 base pairs. Additionally, the phosphoramidite process uses phosphoramidites which are nucleotides modified with protecting groups. Phosphoramidites are expensive and may create artifacts in some applications due to the modifications.

Enzymatic synthesis is a newer technique that addresses some of the deficiencies of the phosphoramidite process. However, the TdT enzyme adds nucleotides in an unregulated manner. Unless controlled, enzymatic synthesis creates unintended homopolymers by repeatedly adding the same nucleotide multiple times. Multiple techniques have been identified to limit homopolymer creation but each increases complexity and comes with its own set of drawbacks.

Alternative ways of creating oligonucleotides that avoid the limitations of current chemical and enzymatic synthesis techniques may find use in multiple applications such as DNA data storage and gene assembly. The following disclosure is made with respect to these and other considerations.

SUMMARY

This disclosure provides methods and devices for assembling oligonucleotides by using a microelectrode array to create localized electric fields that enhance hybridization of oligonucleotide strands in solution to oligonucleotide strands anchored to the surface of the microelectrode array. Selectively applying a positive charge to individual microelectrodes in the microelectrode array attracts negatively-charged oligonucleotides. The oligonucleotide sequences anchored to the microelectrode array, anchor sequences, and the oligonucleotide sequences in solution are designed so that they are at least partially complementary. Hybridization occurs at appreciable levels only in proximity to electrodes that are activated providing spatial control. Different combinations of electrodes may be activated at each round of assembly creating a high degree of parallelism and enabling creation of oligonucleotides with unique sequences.

In an implementation, the oligonucleotides in solution are "oligonucleotide complexes" that include a pre-synthesized payload region encoding arbitrary information or carrying a portion of a gene. Oligonucleotide complexes have a double-stranded (ds) payload region flanked by two single-stranded (ss) sticky ends or overhangs. The payload region may encode any arbitrary value such as a bit ("0" or "1"), a character (A, B, C, D, . . . ), or any other value. The payload region may also encode a sequence that has biological meaning such as all or part of a gene.

One of the sticky ends may hybridize to anchor sequences attached to the surface of the microelectrode array. The other sticky end provides a single-stranded region for a subsequent oligonucleotide complex to hybridize. Oligonucleotide complexes may be added sequentially, each hybridizing to the sticky end created by the previous one. The oligonucleotide complexes hybridized to each other and to the anchor sequence may be stitched together by creating a conventional nucleotide backbone using ligase or by creating an alternative backbone using a click chemistry reaction.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures are schematic representations and items shown in the figures are not necessarily to scale.

DETAILED DESCRIPTION

Figure 1:
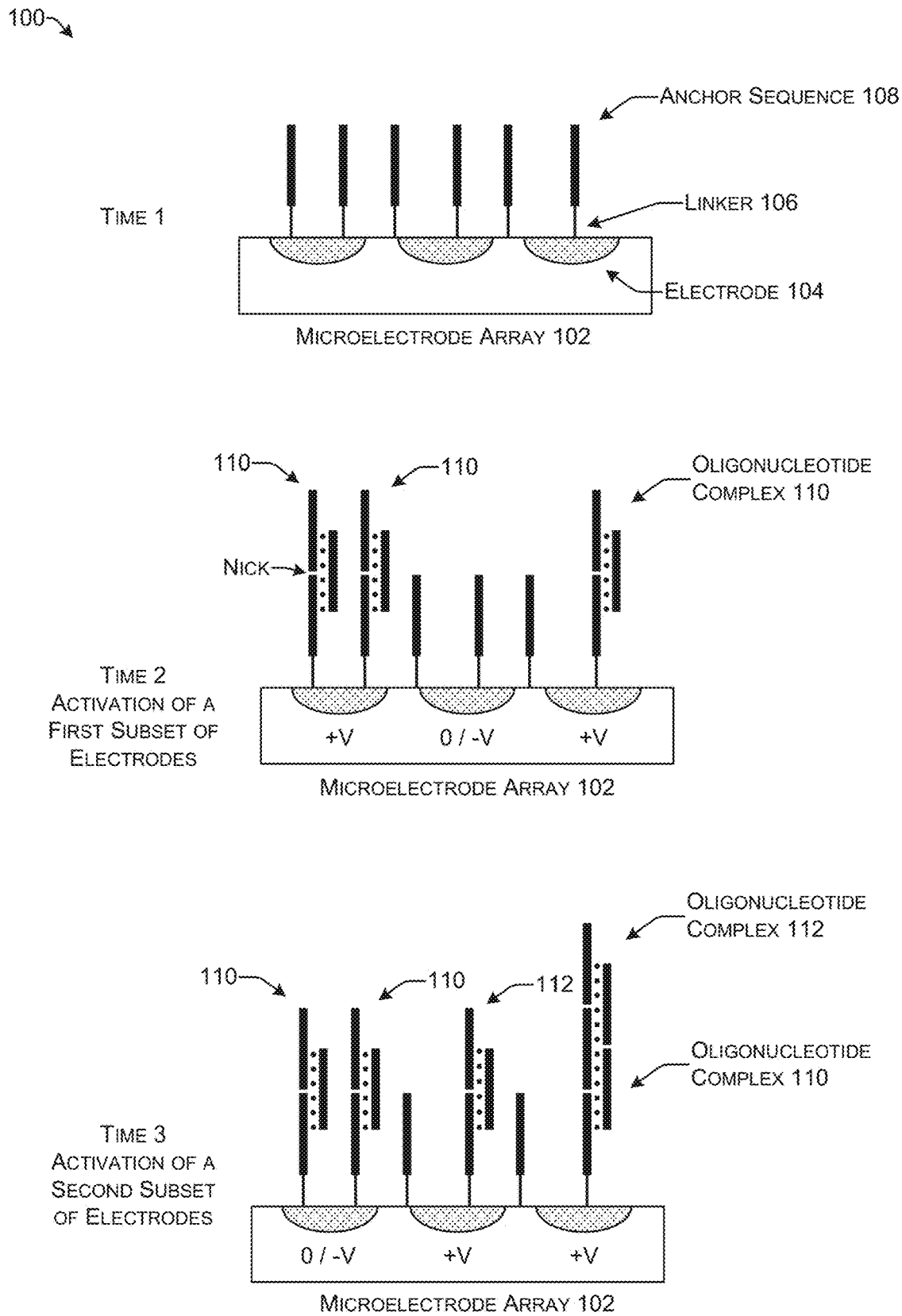
FIG. 1 illustrates creation of oligonucleotides by combining multiple oligonucleotide complexes at locations controlled by selective activation of individual electrodes on a microelectrode array.

This disclosure provides techniques that use electrically controlled hybridization to selectively assemble oligonucleotides with specified, arbitrary sequences. These assembly techniques are alternatives to conventional phosphoramidite oligonucleotide synthesis and enzymatic oligonucleotide synthesis using TdT. The assembly techniques presented in this disclosure are performed in aqueous solution with common reagents. These techniques are readily adapted for automated or semiautomated systems such as microfluidic or laboratory robotics systems and may be used for massively parallel creation of oligonucleotides without generation of organic solvent waste or introduction of undesired homopolymers.

Electrically controlled hybridization or electro-assisted hybridization uses electrodes on a microelectrode array to create positive charges that attract negatively charged oligonucleotides. This attraction pulls the oligonucleotides to only those electrodes that currently have a positive charge and creates a higher localized concentration of oligonucleotides in the solution near each positively charged electrode. This both creates site-selectivity, causing reactions to occur only those electrodes that are activated with a positive charge, and concentrates oligonucleotides in the region of the active electrodes, leading to a higher local concentration which can increase reaction kinetics. Electrodes that are negatively charged or neutral (i.e., no charge) do not attract oligonucleotides.

The microelectrode array is coated with anchor oligonucleotides that are single-stranded oligonucleotides attached to the surface of the microelectrode array through functionalization or by a linker. Many linkers and other techniques for attaching oligonucleotide strands to the surface of a substrate are known to those of ordinary skill in the art. Examples include silane functionalization which covers a surface with organofunctional alkoxysilane molecules or agarose functionalization which covers a surface with polysaccharide matrix. Examples of linkers that may be used are provided in U.S. patent application Ser. No. 16/230,787 filed on Dec. 21, 2018, with the title "Selectively Controllable Cleavable Linkers." Non-covalent attachment such as streptavidin-biotin interactions may also be used to attach the anchor oligonucleotides to the microelectrode array.

The microelectrode array may contain a large number of microelectrodes that make it possible to create many different oligonucleotides (e.g., 10,000, 60,000, 90,000, or more) on the surface of a single array. This high level of multiplexing is made possible in part by the microelectrode density which may be approximately 1000 microelectrodes/cm$^2$, 10,000 microelectrodes/cm$^2$, or a different density. Examples of suitable microelectrode arrays are provided in Bo Bi et al., *Building Addressable Libraries: The Use of "Safety-Catch" Linkers on Microelectrode Arrays*, 132 J. Am. Chem. Soc. 17,405 (2010) and in U.S. patent application Ser. No. 16/435,363 filed on Jun. 7, 2019, with the title "Reversing Bias in Polymer Synthesis Electrode Array."

The anchor oligonucleotides attached to the microelectrode array are extended by iterative addition of pre-synthesized oligonucleotide sequences or individual nucleotides. The oligonucleotides that are available in solution to hybridize with the anchor oligonucleotides may be changed during each round of assembly. This controls "what" is added to the oligonucleotides attached to the microelectrode array. The selection of which electrodes are positively charged controls "where" addition occurs. By varying what is added and where additions occur, it is possible to assemble different oligonucleotides at each electrode on the microelectrode array.

Oligonucleotides, also referred to as polynucleotides, include both deoxyribonucleic acid (DNA), ribonucleic acid (RNA), and hybrids containing mixtures of DNA and RNA. DNA includes nucleotides with one of the four natural bases cytosine (C), guanine (G), adenine (A), or thymine (T) as well as unnatural bases, noncanonical bases, and modified bases. RNA includes nucleotides with one of the four natural bases cytosine, guanine, adenine, or uracil (U) as well as unnatural bases, noncanonical bases, and modified bases.

Unless otherwise specified, hybridization as used throughout this disclosure refers to the capacity for hybridization between two single-stranded oligonucleotides or oligonucleotide segments at 21° C. in 1×TAE buffer containing 40 mM TRIS base, 20 mM acetic acid, 1 mM ethylenediaminetetraacetic acid (EDTA), and 12.5 mM MgCl$_2$. Hybridization and washing conditions are well known and exemplified in Sambrook, J., Fritsch, E. F. and Maniatis, T. *Molecular Cloning: A Laboratory Manual, Second Edition*, Cold Spring Harbor Laboratory Press, Cold Spring Harbor (1989), particularly Chapter 11 and Table 11.1 therein; and also in Sambrook, J. and Russell, W., *Molecular Cloning: A Laboratory Manual, Third Edition*, Cold Spring Harbor Laboratory Press, Cold Spring Harbor (2001). As is known to those of ordinary skill in the art, conditions of temperature and ionic strength determine the "stringency" of the hybridization.

It is understood the sequence of an oligonucleotide need not be 100% complementary to that of its target to be specifically hybridizable. Moreover, the oligonucleotide may hybridize over one or more segments such that intervening or adjacent segments are not involved in the hybridization event (e.g., a loop structure or hairpin structure). The oligonucleotide can comprise at least 20%, at least 30%, at least 40%, at least 50%, at least 60%, at least 70%, at least 80%, at least 90%, at least 95%, at least 99%, or 100% sequence complementarity to a target region within the target oligonucleotide sequence to which they are targeted. The degree to which two oligonucleotides are complementary may also be defined in terms of the number of complementary base pairs. For example, oligonucleotides may be hybridizable if they have at least 5, at least 10, at least 15, at least 20, or more complementary base pairs.

For example, an antisense oligonucleotide in which 18 of 20 base pairs of the antisense compound are complementary to a target region, and would therefore specifically hybridize, would represent 90% complementarity. In this example, the remaining non-complementary nucleotides may be clustered or interspersed with complementary nucleotides and need not be contiguous to each other or to complementary nucleotides. As a further example, two oligonucleotides each with 100 nucleotides may hybridize if they share a region in which 20 base pairs are complementary. Percent complementarity between particular stretches of oligonucleotide sequences can be determined routinely using software such as the BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

FIG. 1 shows an illustrative time series 100 showing creation of oligonucleotides by combining multiple oligonucleotide complexes at locations controlled by selective activation of individual electrodes on a microelectrode array 102. The microelectrode array 102 shown in this time series 100 is illustrated with only three electrodes 104 but it is to be understood that the microelectrode array 102 may have many more electrodes 104. At Time 1, the microelectrode array 102 is shown coated with linkers 106 that are attached to anchor sequences 108 shown here as black bars. The linkers 106 include molecules and structures that attach the anchor sequences 108 to the surface of the microelectrode array 102 such as both linker molecules and functional coatings. A length of the anchor sequences 108 may be between about 5-50, 10-30, 15-20, or 15 nucleotides. All of the anchor sequences 108 on the microelectrode array 102 may have the same nucleotide sequence.

Attachment of the anchor sequences 108 to the surface of the microelectrode array 102 may not correlate in a one-to-one manner with that electrodes 104. Some electrodes 104 may have more than one anchor sequence 108 attached. Some anchor sequences 108 may be attached to a portion of the microelectrode array 102 that does not include an electrode 104. Some electrodes 104 may have no anchor sequences 108 attached (not shown). However, all anchor sequences 108 attached to the same electrode 104 will be exposed to the same electrochemical environment and generate the same oligonucleotides.

At Time 2, a first subset of the electrodes 104 is activated. As used herein, "activation" of an electrode 104 refers to causing the electrode 104 to have a positive charge relative to a reference electrode or to ground. The surface of the microelectrode array 102 may be covered with either an aqueous buffer solution or mixed aqueous/organic solvent system that is electrically conductive. The two positively charged electrodes attract an oligonucleotide complex 110. Oligonucleotide complex 110 is a partially double-stranded structure shown here by two gray bars. One of the single-stranded sticky ends of the oligonucleotide complex 110 hybridizes with the anchor sequence 108. Hybridization resulting in a double-stranded oligonucleotide sequence is indicated by a series of black dots.

After hybridization, the oligonucleotide complex 110 is attached to the anchor sequence 108 by base-pairing interactions between the nucleotide bases. Thus, a nick remains in between the end of the anchor sequence 108 and the strand in the oligonucleotide complex 110 that abuts to the end of the anchor sequence 108.

At time 3, activation of a second subset of electrodes 104 illustrates how a second oligonucleotide complex 112 shown here by a light gray bar and a black bar may be directed to hybridize with a different set of anchor sequences 108. This process may be repeated, iteratively adding additional oligonucleotide complexes 110, 112 to the anchor sequences 108.

Figure 2:
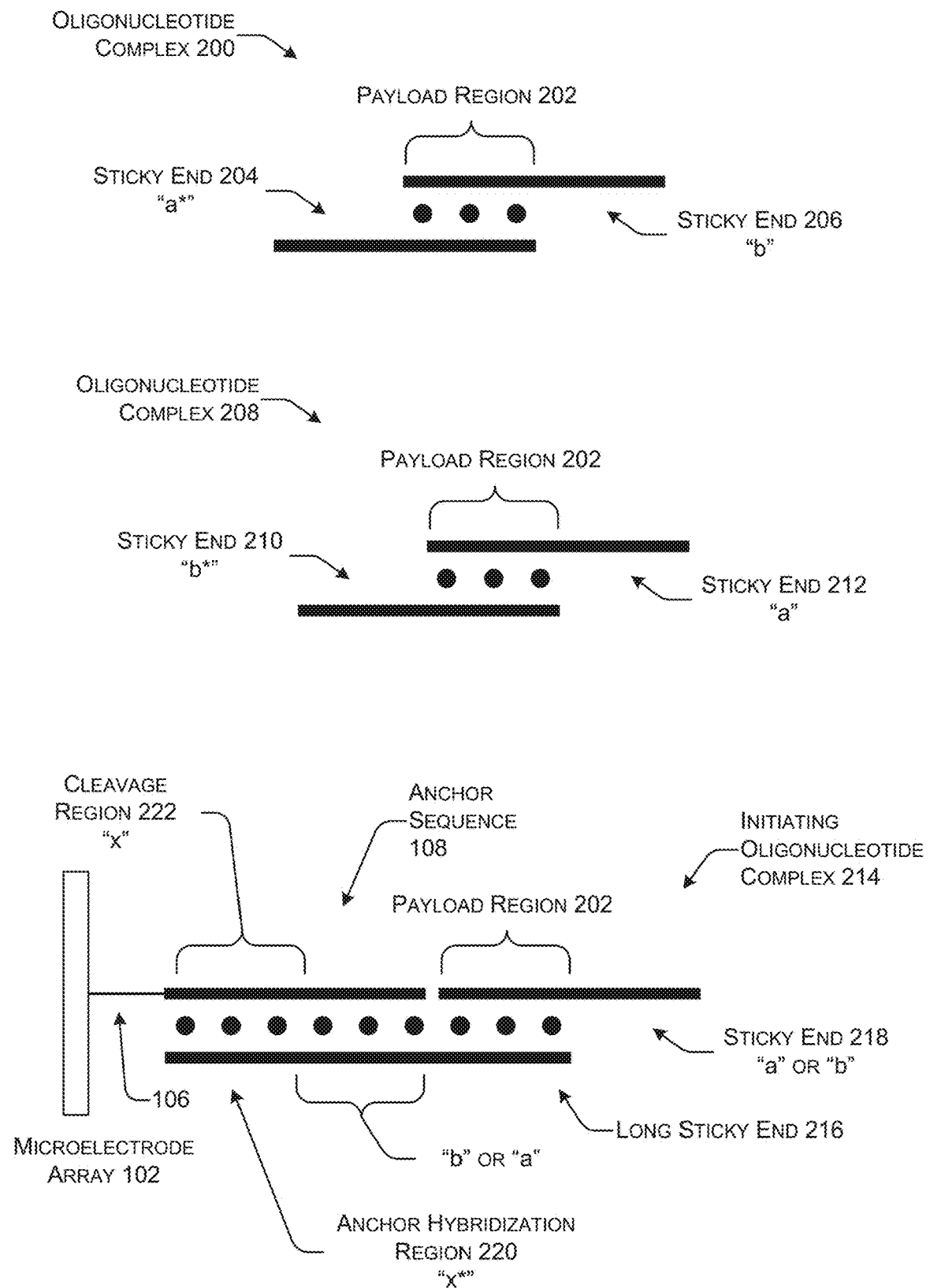
FIG. 2 illustrates configurations of multiple types of oligonucleotide complexes.

FIG. 2 illustrates configurations of multiple types of oligonucleotide complexes. oligonucleotide complex 200 includes a payload region 202 which is the double-stranded region in the middle, although not necessarily centered between the two sticky ends 204 and 206. The payload region 202 may be any length for example between about 1-50 nucleotides, about 10-20 nucleotides, or about 10 nucleotides. The sequence of the payload region 202 may encode an arbitrary value such as a binary digit or a bit with an example encoding of CTA=1 and ACG=0. The payload region 202 may encode trits, letters of the English alphabet or any other arbitrary value. The number of different variations of the payload region 202 may depend on the number of different values that are encoded (e.g., two different payload regions for encoding bits, 26 different payload regions for encoding letters of the English alphabet, etc.). In some implementations, the payload region 202 may also encode sequences with biological meaning such as portions of a gene.

In an oligonucleotide complex 200, the payload region 202 is flanked by the first sticky end 204 and a second sticky end 206. The sticky ends 204 and 206 are not complementary to each other. If they were complementary, oligonucleotide complexes 200 could hybridize with each other in solution forming rings or other structures and preventing efficient hybridization with the anchor sequences 108. The sticky ends 204, 206 may be the same length or different lengths and any length for example between about 5-30 nucleotides, about 10-20 nucleotides, or about 10 nucleotides. Thus, the total length of one single-stranded oligonucleotide in an oligonucleotide complex 200 may be about 6-80 nucleotides, about 20-40 nucleotides, or about 20 nucleotides.

The first sticky end 204 is denoted in the figures as "a*" and the second sticky end 206 is denoted as "b." The notation of n* indicates a sequence that hybridizes to or is complementary to n where n represents a single-stranded oligonucleotide sequence. Thus, a* is complementary to sequence a, b* is complementary to sequence b, and so forth.

The second oligonucleotide complex 208 shown in FIG. 2 contains the same payload region 202 but with a first alternate sticky end 210 (e.g., b*instead of b) and a second alternate sticky end 212 (e.g., a*instead of a) that are complementary to the sticky ends 204 and 206 of the first oligonucleotide complex 200. The oligonucleotide complex 208 may be referred to as an alternate configuration of the first oligonucleotide complex 200 or as a complementary oligonucleotide complex. This alternate configuration of the first oligonucleotide complex 200 includes the alternate sticky ends 210 and 212.

Due to the inclusion of a washing step between rounds of assembly, the two complementary oligonucleotide complexes 200, 208 are generally not in solution together. However, after either of the oligonucleotide complexes 200, 208 are hybridized to anchor sequences 108, they will remain after washing and provide a sticky end to hybridize with the next oligonucleotide complex. Yet, because the oligonucleotide complexes 200, 208 do not hybridize to themselves, a complementary oligonucleotide complex is used.

If the same payload region 202 is added twice, for example to encode the binary string 00, the oligonucleotide complex 200 could not be used to add the second 0 because the two sticky ends 204 and 206 are noncomplementary. If the sticky end with the sequence a* hybridizes to an anchor sequence 108, then the available sticky end for the next oligonucleotide complex to hybridize will have sequence b. But oligonucleotide complex 200 does not have a sticky end with sequence b*. Thus, the complementary oligonucleotide complex 208 is used. The version of the oligonucleotide complex 200, 208 is alternated for each round of assembly.

In some implementations, the oligonucleotide complex that hybridizes to the anchor sequence 108, the "initiating oligonucleotide complex" 214, may be different than oligonucleotide complexes used later in assembly. The initiating oligonucleotide complex 214 is a partially double-stranded structure and may have a long sticky end 216 that hybridizes to the anchor sequence 108 and a regular-length sticky end 218. The long sticky end 216 may hybridize to the full length of the anchor sequence 108. The long sticky end 216 may include a region that has the same sequence as a sticky end of other oligonucleotide complexes 200, 208 (e.g., an "a," "b," "a*," or "b*" sequence) and an anchor hybridization region 220 "x*" that hybridizes to a cleavage region 222 in the anchor sequence 108 denoted as "x". Use of a long sticky end 216 creates a longer region of hybridization with the anchor sequence 108 which can increase stability. However, the long sticky end 216 does not necessarily include a region that hybridizes to a sticky end (i.e., no "a" or "b" sequence) and may instead include the anchor hybridization region 220 alone or together with a nucleotide sequence that hybridizes only to the anchor sequence 108.

The long sticky end 216 can create a double-stranded region that is not found elsewhere. This double-stranded region is formed from the hybridization of the cleavage region 222 and the anchor hybridization region 220 and be located at or near the base of the anchor sequence 108 as shown in FIG. 2. This cleavage region 222 provides a unique sequence for recognition and cleavage by enzymes such as Type II restriction enzymes or Cas9. Thus, a length of the cleavage region 222 may be at least a length sufficient to be recognized by an endonuclease such as, for example at least four, five, six, seven, eight, nine, or 10 nucleotides. Enzymatic cleavage of the anchor sequence 108 is one technique for separating completed oligonucleotides from the microelectrode array 102.

Figure 3:
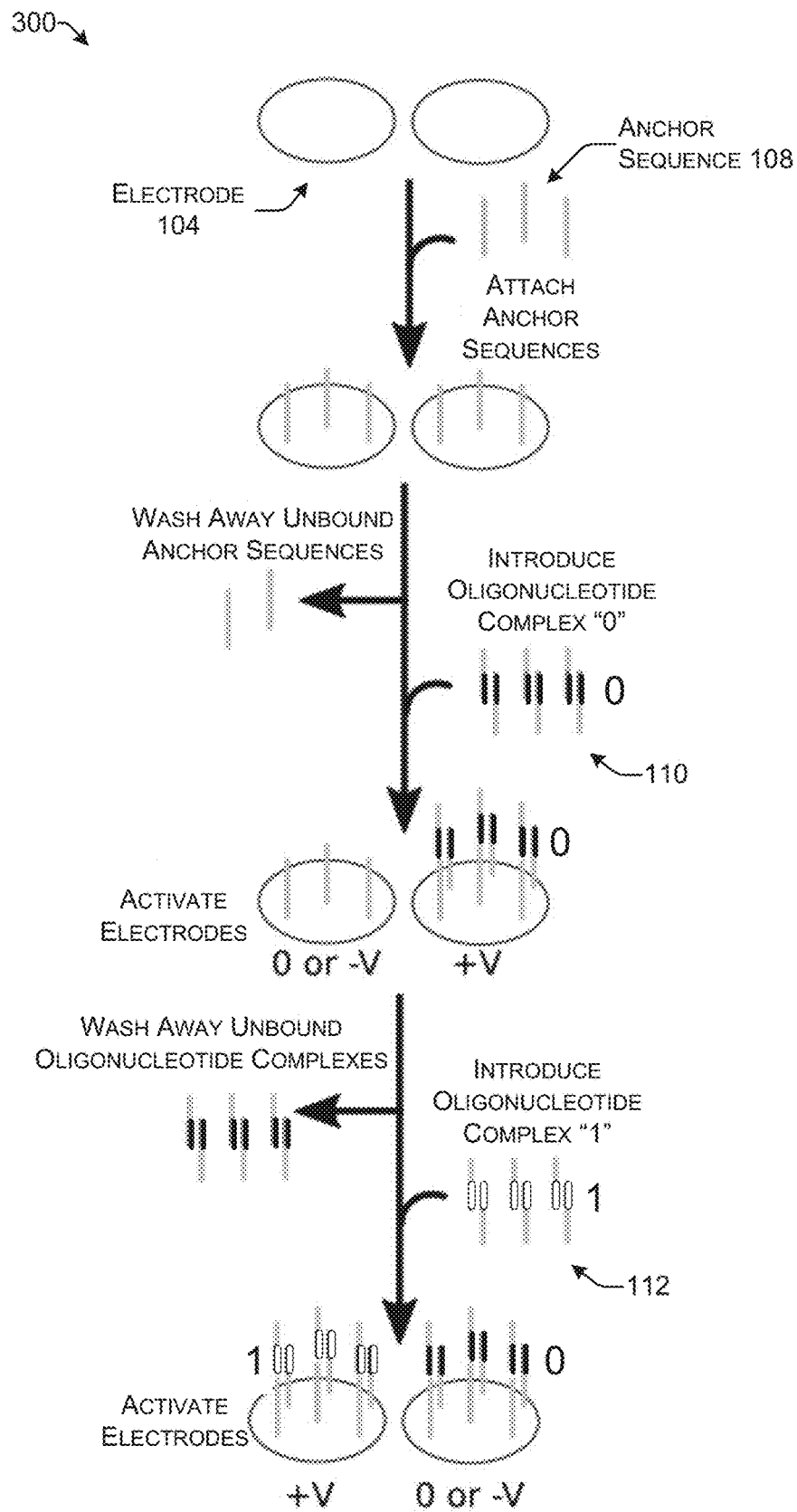
FIG. 3 illustrates a series of steps used to encode arbitrary values at specific locations on the surface of a microelectrode array through the use of multiple oligonucleotide complexes.

FIG. 3 shows a schematic illustration 300 of a series of steps that may be used to encode arbitrary values at specific electrodes 104 on a microelectrode array 102. Prior to selective assembly of oligonucleotides on a microelectrode array 102, the anchor sequences 108, shown here as gray bars, are attached to electrodes 104 on the surface of the microelectrode array 102. The anchor sequences 108 may be created by any known technique for oligonucleotide synthesis and attached to the electrodes 104 by any known technique for anchoring single-stranded oligonucleotides to a solid substrate. Unbound anchor sequences 108 that remain in solution may be washed away during a washing step that may flood the surface of the microelectrode array 102 with water or a predominantly aqueous solution such as a buffer.

In this example, the first oligonucleotide complex 110 introduced to the surface of the microelectrode array 102 encodes the bit "0." However, the payload region of this oligonucleotide complex 110 may, of course, encode a sequence representing any other arbitrary value. Selective activation of electrodes 104 attracts the oligonucleotide complex 110 to only those electrodes that have a positive charge. Thus, although the first oligonucleotide complex 110 is present in solution across the entire surface of the microelectrode array 102, it hybridizes in appreciable amounts only to those anchor sequences 108 attached to activated electrodes. There may, of course, be some minimal amount of hybridization to anchor sequences 108 that are not attached to positively charged electrodes 104.

A subsequent washing step washes away any unbound oligonucleotide complexes 110. Thus, only those oligonucleotide complexes 110 that have hybridized to an anchor sequence 108 remain. As discussed above, hybridization does not require fully complementary sequences but only that the strength of attachment between the oligonucleotide complexes 110 and the anchor sequences 108 is sufficient to hold the oligonucleotide complexes 110 in place during the washing step.

Next, in this example, a second oligonucleotide complex 112 is introduced. This oligonucleotide complex 112 encodes the bit "1." This second oligonucleotide complex 112 has sticky ends with sequences such that it may bind either to the anchor sequences 108 or to the free sticky ends on the first oligonucleotide complex 110. The location of hybridization is controlled by activation of the electrodes. In this example, a different subset of electrodes is activated when the second oligonucleotides complex 112 is available in solution, thus, the second oligonucleotide complex 112 hybridizes to different anchor sequences 108 than the first oligonucleotide complex 110.

Although only two electrodes 104 are shown in this example, this technique of selectively activating specific sets of electrodes while sequentially providing oligonucleotide complexes 110, 112 may be used to create assemblies of oligonucleotide complexes 110, 112 on the surface of individual electrodes 104. Thus, different oligonucleotide sequences each encoding an arbitrary string of bits may be created at each electrode 104.

Figure 4:
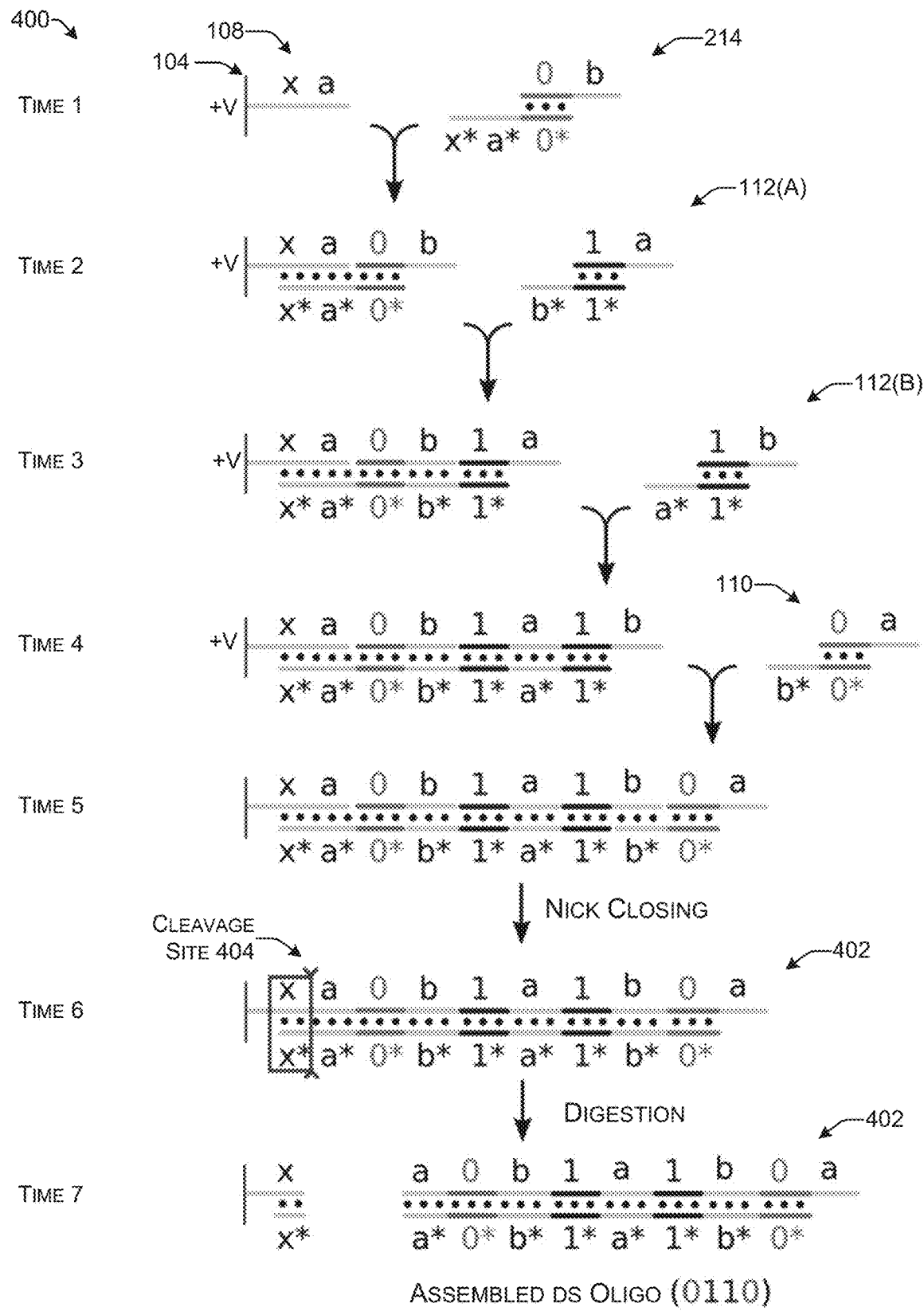
FIG. 4 illustrates a series of steps used to assemble a double-stranded oligonucleotide that encodes a string of arbitrary values and to separate the assembled double-stranded oligonucleotide from the surface of a microelectrode array.

FIG. 4 shows a time series 400 of a series of steps that may be used to encode a string of arbitrary values in an oligonucleotide by creating an ensemble of oligonucleotide complexes. This time series 400 continues with the example of FIG. 3 that uses oligonucleotide complexes to encode bits. FIG. 4 shows the steps of building an oligonucleotide on a single electrode 104. The same steps may be repeated for other electrodes 104 on a microelectrode array 102 to create oligonucleotides with different sequences.

At Time 1, an anchor sequence 108 with the sequence represented by "x a" is shown attached to the electrode 104. An initiating oligonucleotide complex 214 is introduced. This initiating oligonucleotide complex 214 encodes the bit "0." The electrode 104 has a positive charge which attracts the oligonucleotide complex 214 to the proximity of the anchor sequence 108.

At Time 2, a first version of an oligonucleotide complex 112(A) encoding the bit "1" is introduced. This is followed at Time 3 by the introduction of a third oligonucleotide complex which may be thought of as a second version of the oligonucleotide complex 112(B) that also encodes the bit "1." The first and second versions of this oligonucleotide complex 112 include the same payload region encoding the same arbitrary value of 1 but have different sticky ends. The difference in the sticky ends makes it possible for the sticky end "a*" on the second version of the oligonucleotide complex 112(B) to hybridize with the available sticky end "a" on the first version of the oligonucleotide complex 112(A). The third oligonucleotide complex in this example encodes the bit "1" but the third oligonucleotide could also encode the bit "0" with the same alternate sticky ends and only a different payload region.

At Time 4, an oligonucleotide complex 110 encoding the bit "0" is introduced. This oligonucleotide complex 110 may also be available in two different versions that have different, and complementary sticky ends. The version with a sticky end that is capable of hybridizing to the available sticky end "b" on the oligonucleotide complex 112(B) that was most recently added is used. This is illustrated by the sticky-end labeled with "b*." This process of sequentially adding oligonucleotide complexes that encode arbitrary values such as 0 or 1 may be repeated until the desired sequence of data (e.g., a string of bits) is represented in the oligonucleotide.

At Time 5, there is an ensemble of oligonucleotide complexes hybridized to each other and ultimately to the anchor sequence 108. However, the structure is held together only by the base-pairing interactions of the hybridized nucleotide bases. At this point, nicks in the backbone of the oligonucleotides have not been closed. Nicks in an oligonucleotide backbone may be closed by ligation. Techniques for performing ligation and closing of nicks in DNA and RNA are well-known to those of ordinary skill in the art.

Ligases for both DNA and RNA are known. DNA ligase is a specific enzyme that joins DNA strands together by catalyzing the formation of a phosphodiester bond. One specific type of DNA ligase that is frequently used in molecular biology is T4 DNA Ligase isolated from bacteriophage T4. T4 DNA ligase is most active at 37° C. RNA ligase (ATP) is an analogous enzyme that catalyzes the formation of phosphodiester bonds between ribonucleotides. One commercially available RNA ligase suitable for closing nicks is T4 RNA ligase 2. T4 RNA ligase 2 is also most active at 37° C.

However, for optimal ligation efficiency with sticky ends, the optimal temperature for the enzyme is balanced with the melting temperature $T_m$ of the sticky ends being ligated because the homologous pairing of the sticky ends may be disrupted by high temperatures. If any of the sticky ends in the double-stranded oligonucleotide structure shown at Time 5 would be disrupted at optimal temperatures for the selected ligase, a lower temperature may be used. Persons of ordinary skill in the art will understand how to calculate $T_m$ for a given oligonucleotide structure and adjust the ligation temperature appropriately.

Another technique for closing nicks uses click chemistry to form covalent bonds between nucleotides with modified 3-end 5'-ends. One click-chemistry reaction that may be used is Copper(I)-catalyzed azide-alkyne cycloaddition (CuAAC) also referred to as azide-alkyne Huisgen cycloaddition. With this reaction, an alkyne and an azide group are joined by a cycloaddition reaction to form a triazole unit that becomes the backbone connecting adjacent nucleotides. This reaction is triggered by addition of copper(I). Use of CuAAC to join DNA strands is discussed in El-Sagheer and Brown, *Click Nucleic Acid Ligation: Applications in Biology and Nanotechnology*, 45(8) Accounts of Chem. Res. 1258 (2011).

Closing of the nicks creates an assembled double-stranded oligonucleotide 402. This assembled double-stranded oligonucleotide 402 is separated from the electrode 104 at Time 6 by digestion with an endonuclease. This cleavage site 404 is created by the double-stranded sequence formed through hybridization of the initiating oligonucleotide complex 214 with the anchor sequence 108. Cleavage may be performed using conventional techniques for restriction enzyme or Cas9 digestion with conditions selected based on the endonuclease used to cut the double-stranded oligonucleotide.

The assembled double-stranded oligonucleotide 402 is freed from the electrode 104 at Time 7. A string of binary digits (e.g., 0110) is encoded in both strands of the assembled double-stranded oligonucleotide 402. The assembled double-stranded oligonucleotide 402 may be denatured and amplified by polymerase chain reaction (PCR) to create additional copies. It may be stored as a molecular record of the binary digits. Thus, the assembled double-stranded oligonucleotide 402 may function as a medium for storing digital data. The information or data encoded in the assembled double-stranded oligonucleotide 402 may be read by sequencing either or both strands.

Figure 5:
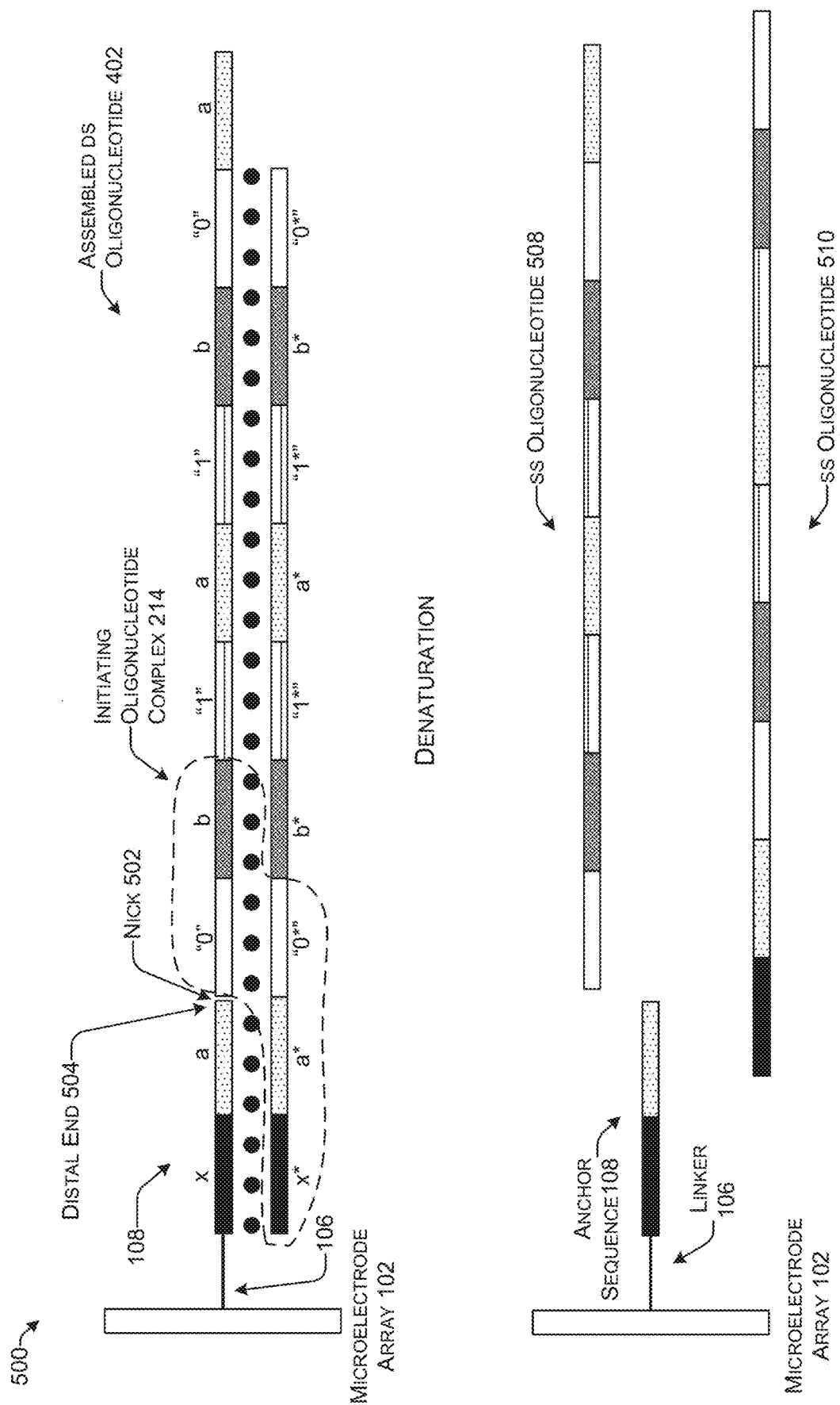
FIG. 5 illustrates a technique for separating an assembled double-stranded oligonucleotide from the surface of the microelectrode array by denaturation.

FIG. 5 shows a diagram 500 of a technique for separating an assembled double-stranded oligonucleotide 402 from the surface of a microelectrode array 102 by denaturation. FIG. 4 shows separation of the double-stranded oligonucleotide 402 by digestion with an endonuclease. However, an alternative technique intentionally leaves a nick 502 at the end of the anchor sequence 108. Because of this nick 502, the assembled double-stranded oligonucleotide 402 is not covalently attached to the anchor sequence 108.

In order for a ligase to form a phosphodiester bond between adjacent nucleotides, there must be a 5'-phosphate group. Intentional omission of the 5'-phosphate group prevents the nick 502 from being closed. The anchor sequence 108 may be attached to the microelectrode array 102 in any orientation, so the distal end 504 of the anchor sequence 108 may be the 5'-end or the 3'-end. If the distal end 504 of the anchor sequence 108 is the 5'-end, then the anchor sequence 108 may be created without a 5'-phosphate group. Alternatively, if the distal end 504 of the anchor sequence 108 is the 3'-end, then the 5'-end adjacent to the nick 502 is provided by the initiating oligonucleotide complex 214. The initiating oligonucleotide complex 214 may be created so that it lacks a 5' phosphate on the end of the payload region that abuts the anchor sequence 108.

With these modifications, creation of the assembled double-stranded oligonucleotide 402 may proceed as shown in FIG. 4. However, due to the lack of a 5'-phosphate group, the nick 502 is not closed during the ligation step. Thus, denaturation will free the assembled double-stranded oligonucleotide 402 from the anchor sequence 108 and separate it into a first single-stranded oligonucleotide 508 and a second single-stranded oligonucleotide 510. The single-stranded oligonucleotides 508 and 510 may be washed away from the surface of the microelectrode array 102 and the anchor sequence 108 may be reused. Denaturing may be performed by any suitable technique including, but not limited to, heating above the $T_m$ of the assembled double-stranded oligonucleotide 402, adding sodium hydroxide, and increasing the salt concentration. These and other techniques for denaturing double-stranded oligonucleotides are well-known to those of ordinary skill in the art.

If click chemistry is used to close nicks, the nick 502 may be created through analogous modifications that omit one or both of an azide group or an alkyne group from either the distal end 504 of the anchor sequence 108 or the initiating oligonucleotide complex 214. Lack of the required group prevents the cycloaddition reaction at this location thus leaving the nick 502.

Figure 6:
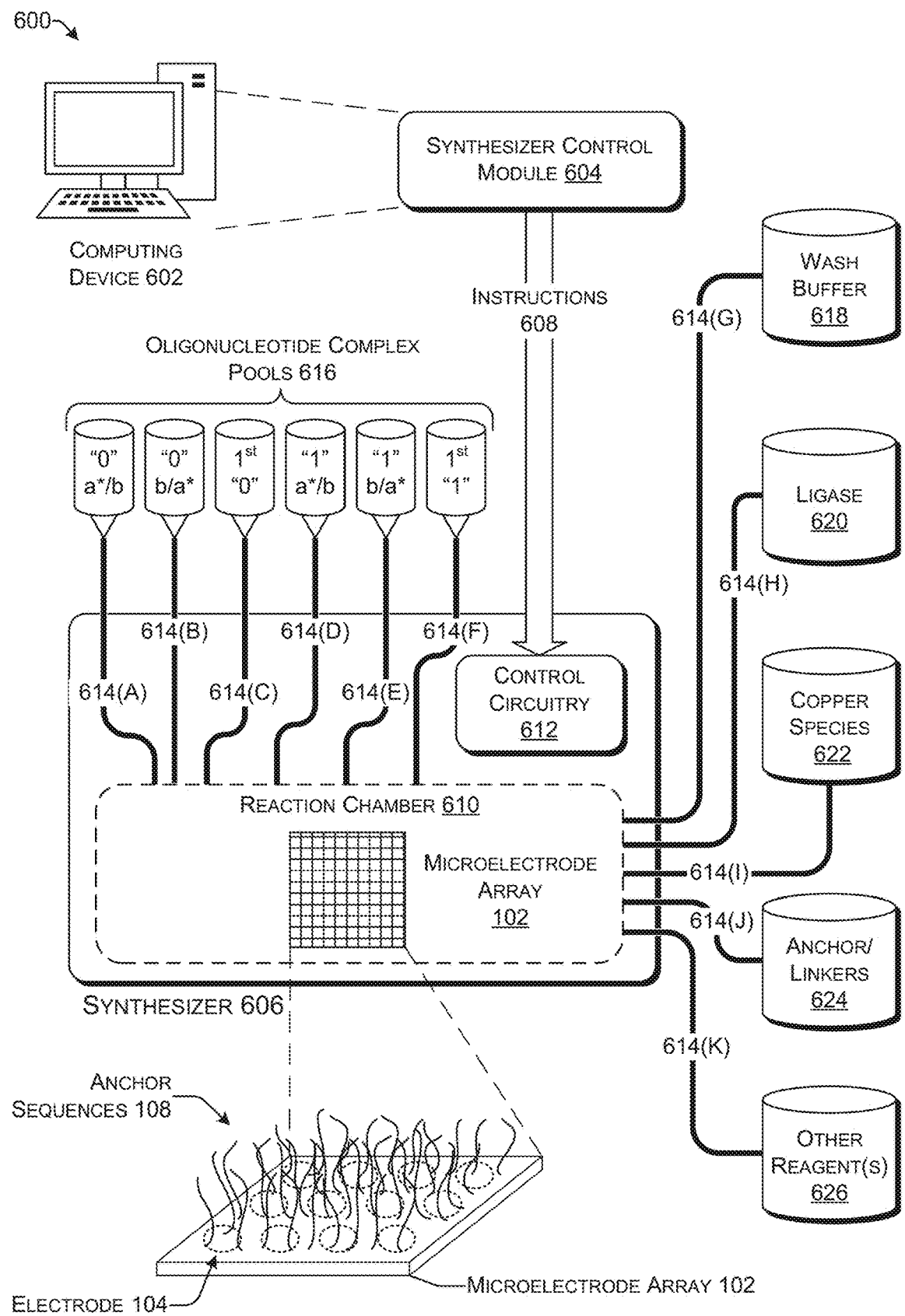
FIG. 6 is an illustrative system for creating oligonucleotides by joining multiple oligonucleotide complexes together.

FIG. 6 shows an illustrative system 600 that may include a computing device 602 with a synthesizer control module 604 that is communicatively connected to a synthesizer 606. The synthesizer control module 604 may provide instructions 608 that control the operation of the synthesizer 606. The instructions may cause the synthesizer 606 to create oligonucleotides with specific sequences and/or that encode specific information. The computing device 602 may be implemented as any type of conventional computing device such as a desktop computer, a laptop computer, a server, a hand-held device, or the like. In an implementation, the computing device 602 may be a part of the synthesizer 606 rather than a separate device.

The synthesizer 606 is a device that selectively assembles oligonucleotides through electrically controlled hybridization. The microelectrode array 102 may be located within a reaction chamber 610 or container capable of maintaining an aqueous or predominantly aqueous environment in contact with the surface of the microelectrode array 102. The synthesizer 606 may also include a heater to control the temperature of aqueous solution in the reaction chamber 610.

As described above, the microelectrode array 102 includes a plurality of electrodes 104 that are able to be independently activated to vary the charge across the surface of the microelectrode array 102. In one example implementation, the microelectrode array 102 is functionalized by spin coating with a 3 wt % solution of agarose in 1×TBE buffer for 30 s at 1500 rpm. After coating, the microelectrode array 102 is baked at 50° C. for 1 h. This creates a surface with functional groups that can bind to the anchor sequences 108. The anchor sequences 108 may be synthesized directly onto the agarose coating using standard phosphoramidite reagents and methods. After preparation by this, or another, technique, the microelectrode array 102 may be placed in the synthesizer 606.

Control circuitry 612 may control the operation of the synthesizer 606. The control circuitry 612 may be implemented as any type of circuitry suitable for controlling hardware devices such as a printed circuit board, microcontroller, a programmable logic controller (PLC), or the like. The control circuitry 612 receives the instructions 608 provided by the synthesizer control module 604. Instructions 608 may indicate the order of nucleotides that are to be assembled at individual electrodes 104 on the microelectrode array 102. The control circuitry 612 may be able to independently control the voltage at each of the electrodes 104 in the microelectrode array 102. The control circuitry 612 may also be able to activate fluid delivery pathways 614 that control movement of fluids throughout the synthesizer 606 including in the reaction chamber 610. The fluid delivery pathways 614 may be implemented by tubes and pumps, microfluidics, laboratory robotics, or other techniques known to those of ordinary skill in the art.

Microfluidic technology facilitates the automation of chemical and biological protocols. These devices manipulate small quantities of liquid at smaller scales and with higher precision than humans. Digital microfluidic (DMF) technology is one type of flexible microfluidic technology. DMF devices manipulate individual droplets of liquids on a grid of electrodes, taking advantage of a phenomenon called electrowetting on dielectric. Activating electrodes in certain patterns can move, mix, or split droplets anywhere on the chip. Microfluidics also include full-stack microfluidics which are programmable systems that allow unrestricted combination of computation and fluidics. Examples of microfluidic technology may be found in Willsey et al., *Puddle: A dynamic, error-correcting, full-stack microfluidics platform*, Aplos'19, April 13-17, 183 (2019).

In an implementation, the synthesizer 606 may include multiple oligonucleotide complex pools 616. The oligonucleotide complexes may be pre-made using any oligonucleotide synthesis technique such as phosphoramidite synthesis and stored in the pools 616 where they are available to be transferred by fluid delivery pathways 614 to the reaction chamber 610. The oligonucleotide complexes may be stored in the pools 616 in an aqueous solution that uses a standard buffer for storing oligonucleotides. The concentration of oligonucleotide complexes in the pools 616 may be, for example, about 0.5, 1, 2, 3, 4, 5, 10, 15, 20, 30, or 50 nM.

There may be one or more pools 616 for each unique payload region encoded by the oligonucleotide complexes. For example, if the oligonucleotide complexes encode bits there will be one set of oligonucleotide complexes that encode "0" and another set of oligonucleotide complexes that include "1." In one implementation, each bit is represented by one of three different oligonucleotide complexes. The bit "0" may be encoded by two complementary oligonucleotide complexes that each contain the same payload sequence but with different and complementary sticky ends. These oligonucleotide complexes are represented as "0" a*/b and "0" a/b*. These may be the same as the oligonucleotide complexes 200 and 208 shown in FIG. 2. There may also be an initiating oligonucleotide complex with a payload encoding "0" represented here as $1^{st}$ "0." This may be the same as the initiating oligonucleotide complex 214 shown in FIG. 2.

Similarly, three different sets of oligonucleotide complexes may be used to encode "1." Thus, six different types of oligonucleotide complexes may be needed to encode two different arbitrary values. If the oligonucleotide complexes are used to encode more than two different arbitrary values such as encoding trits or letters of the English language than the number of oligonucleotide complex pools 616 will increase accordingly. Oligonucleotide complexes from each of the pools 616 may be moved into the reaction chamber 610 through a separate fluid delivery pathway 614(A), 614(B), 614(C), 614(D), 614(E), and 614(F).

One or more of a wash buffer 618, ligase 620, copper species 622, anchor/linkers 624, and other reagent(s) 626 may also be available in pools connected to the reaction chamber 610 by respective fluid delivery pathways 614(G), 614(H), 614(I), 614(J), and 614(K). The wash buffer 618 may include any wash buffer suitable for washing or manipulating oligonucleotides such as TE, TAE, and TBE. The wash buffer may be an aqueous buffer solution or mixed aqueous/organic solvent. Examples of organic solvents that may be added to a wash buffer include polar, miscible organic cosolvents (e.g., DMSO, acetonitrile, etc.) which may be helpful in removing metal ions, organic residues, and denatured protein. The pool of ligase 620 may include DNA ligase and RNA ligase in appropriate buffer concentration for use in closing nicks in oligonucleotides within the reaction chamber 610.

The copper species 622 may be copper(I) that can be added to the reaction chamber 610 to activate the CuAAC reaction. In an implementation, the copper species 622 may be copper(II) which does not activate the CuAAC reaction. Following addition of copper(II) to the reaction chamber 610, it may be reduced at activated electrodes to copper(I) which then triggers the CuAAC reaction. Reduction may be performed globally across the entire surface of the microelectrode array 102 by activating all or substantially all of the electrodes 104. Alternatively, site-selective reduction may be performed by activating only some of the electrodes 104. This restricts the CuAAC reaction to only those electrodes 104 that are activated thereby controlling where formation of a triazole backbone occurs.

The anchors/linkers 624 may be used for preparing the microelectrode array 102 in the reaction chamber 610. This pool may include linkers 106 and/or anchor sequences 108. There may also be one or more additional pools or reservoirs that contain one or more other reagent(s) 626 such as intercalating fluorescent dyes used to detect double-stranded oligonucleotides.

Figure 7:
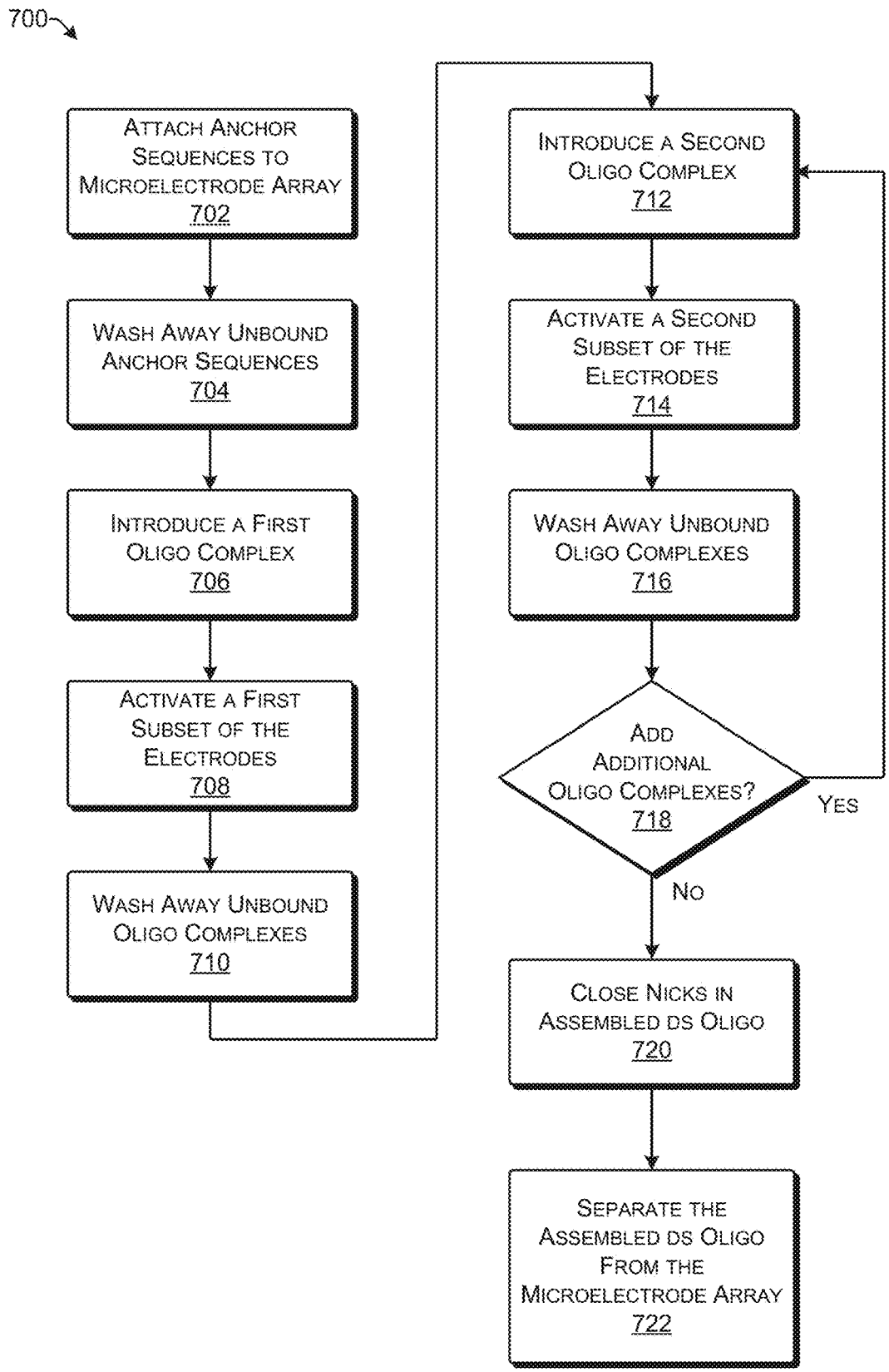
FIG. 7 is a flow diagram showing an illustrative process for assembling a double-stranded oligonucleotide by joining multiple oligonucleotide complexes together.

FIG. 7 shows process 700 for assembling a double-stranded oligonucleotide by joining multiple oligonucleotide complexes together. Process 700 may be implemented, for example, using any of the techniques or systems shown in FIGS. 1-6.

At operation 702, anchor sequences are attached to a microelectrode array. The anchor sequences may be attached to the microelectrode array by any conventional technique for attaching oligonucleotide sequences to a solid substrate. For example, the surface of the microelectrode array may be coated with linker molecules that in turn attach to an end of the anchor sequences. As a further example, the surface of the microelectrode array may be functionalized through silanization or coating with agarose. This creates a microelectrode array that is coated with a plurality of anchor sequences.

At operation 704, unbound anchor sequences are washed away. This removes any anchor sequences that are not attached to the microelectrode array. This washing step may be performed with water or an aqueous wash buffer.

At operation 706, a first oligonucleotide complex is introduced into a reaction chamber containing the microelectrode array. The first oligonucleotide complex encodes a first arbitrary value such as, for example, a first binary digit such as 0. The first oligonucleotide complex is now present in solution across the surface of the microelectrode array. One of the two non-complementary sticky ends of the first oligonucleotide complex is complementary to and can hybridize with at least a portion of the anchor sequences.

At operation 708, a first subset of electrodes in the microelectrode array is activated. Activation of the electrodes applies a positive charge which attracts the negatively charged oligonucleotide complexes. In one implementation, a voltage of +3.3 V may be applied for three cycles of 60 s with 10 s at 0 V between each cycle. Without being bound by theory, this length and duration of activation may provide the oligonucleotide complexes with sufficient time to migrate to the electrodes and hybridize to the anchor sequences. Activation of the first subset of electrodes attracts the first oligonucleotide complex to a first subset of anchor sequences that are attached the microelectrode array at the locations of the first subset of electrodes.

At operation 710, unbound oligonucleotide complexes may be washed away with the aqueous solution such as water or a buffer. Thus, only those oligonucleotide complexes that have hybridized to an anchor sequence remain in the reaction chamber.

At operation 712, a second oligonucleotide complex encoding a second arbitrary value is introduced into the reaction chamber. The second oligonucleotide complex includes a sticky end that is homologous to a sticky end of the first oligonucleotide complex that did not hybridize to the anchor sequence (e.g., the free sticky end). The second oligonucleotide complex encodes a second arbitrary value, for example, a second binary digit such as 1. Although this example process 700 describes adding two different arbitrary values in series, it is also possible to add the same arbitrary value repeatedly (e.g., to encode 000 or 111).

At operation 714, a second subset of electrodes in the microelectrode array is activated. Activation of the second subset of electrodes attracts the second oligonucleotide complex to the surface of the microelectrode array where it may hybridize with an anchor sequence or with one of the first oligonucleotide complexes that have already hybridize to an anchor sequence. The second subset of electrodes may include electrodes that were activated with the first subset of electrodes at operation 708. Alternatively, the second subset of electrodes may have no overlap with the first subset of electrodes. Activation of the second subset of electrodes attracts the second oligonucleotide complex to a second subset of anchor sequences that are attached the microelectrode array at the locations of the second subset of electrodes.

At operation 716, unbound oligonucleotide complexes may be washed away with the aqueous solution such as water or a buffer. Thus, only those ones of the first oligonucleotide complex and the second oligonucleotide complex that have hybridized to either the anchor sequences or another oligonucleotide complex remain in the reaction chamber.

At operation 718, it is determined if additional oligonucleotide complexes will be added. This determination may be made, for example, by the synthesizer control module 604 and/or the control circuitry 612 shown in FIG. 6. Additional oligonucleotide complexes may be subsequently added until the desired string of values is represented in the oligonucleotide hybridized to the microelectrode array. For example, in the example shown in FIG. 4, the desired string of values is 0110. Once the fourth oligonucleotide complex encoding the final 0 has been added, assembly is complete and there is no need to add additional oligonucleotide complexes.

If the desired sequence has not been fully assembled, then process 700 proceeds along the "yes" path and returns to 712 where a third oligonucleotide complex with alternate sticky ends may be introduced to the reaction chamber. The third oligonucleotide complex may be drawn to a third subset of electrodes that are subsequently activated. Control which oligonucleotide strands incorporate the third oligonucleotide complex is achieved by controlling which electrodes are activated in the third subset of electrodes and the value encoded is controlled by the payload sequence of the third oligonucleotide complex. Repeated cycles of adding nucleotide complexes and activating selected subsets of electrodes enable the creation of multiple different oligonucleotides with specified sequences of the arbitrary values encoded by the oligonucleotide complexes. If, however, no more oligonucleotides will be added, process 700 proceeds along the "no" path to 720.

At operation 720, nicks are closed in the assembled double-stranded oligonucleotides that are attached to the surface of the microelectrode array. Prior to closing the nicks, there is an assembly of multiple oligonucleotide complexes held together by hybridization. One oligonucleotide complex in each double-stranded oligonucleotide provides attachment to the microelectrode array by hybridization to an anchor sequence. For example, some of the double-stranded oligonucleotides are formed from hybridization of the first oligonucleotide complex to the first subset of anchor sequences. Other ones of the double-stranded oligonucleotides may be formed from hybridization of the second oligonucleotide complex to the second subset of anchor sequences.

The nicks may be closed by any of the techniques discussed previously such introducing a ligase into the reaction chamber or initiating Cu(I)-catalyzed azide-alkyne cycloaddition (CuAAC). Closing of the nicks creates continuous backbones on both strands of the assembled double-stranded oligonucleotide. Closing of nicks may be performed only once after the assembled double-stranded nucleotide is complete. However, the stability provided by creating a continuous backbone may improve yields and prevent assembled double-stranded oligonucleotides from denaturing before assembly is complete. Accordingly, operations to close nicks, such as ligation, may be performed periodically throughout assembly such as, for example, after addition of every $10^{th}$ oligonucleotide complex. Nicks may be closed as frequently as after addition of every individual oligonucleotide complex. The specific frequency with which nicks are closed during the assembly of an oligonucleotide complex may be tuned in practice based on reaction conditions and results achieved.

At operation 722, the assembled double-stranded oligonucleotide is separated from the microelectrode array. All assembled double-stranded oligonucleotides attached to the surface of the microelectrode array may be separated in the same operation. Thus, in an implementation, separation of the double-stranded oligonucleotides is not selective. The system 600 may send instructions indicating completion of oligonucleotide assembly to the control circuitry 612. Upon receipt of these instructions, the control circuitry 612 may cause the synthesizer 606 to release the assembled double-stranded oligonucleotides from the microelectrode array 102. In one implementation, the microelectrode array 102 may include heaters such as resistive elements embedded underneath the electrodes. The heaters may be used to raise the temperature causing the double-stranded oligonucleotides to denature and separate from the microelectrode array 102.

There are multiple ways to separate an assembled double-stranded oligonucleotide from the microelectrode array. The support-bound oligonucleotide may be treated with ammonia to cleave a linker. Depending on the type of linker, the treatment may be exposure to gaseous ammonia, aqueous ammonium hydroxide, aqueous methylamine, or a solution of ammonia in anhydrous methanol. Enzymatic cleavage may be used to cut a portion of a double-stranded oligonucleotide in the anchor sequence as shown in FIG. 4. Intentionally leaving a nick at the end of the anchor sequence followed by denaturation may be used to separate a double-stranded oligonucleotide sequence from the microelectrode array as shown in FIG. 5. Cleavage of a linker attaching the anchor sequence to the microelectrode array may be used to separate the assembled double-stranded oligonucleotide (together with anchor sequence) from the microelectrode array. Cleavable linkers and techniques for cleaving such linkers are known to those of ordinary skill in the art.

Following separation from the microelectrode array, the double-stranded oligonucleotide may be processed further such as, for example, by denaturation and amplification with PCR. The PCR product may be stored for short- or long-term. The sequence arbitrary values encoded in the double-stranded oligonucleotide may be obtained by sequencing the double-stranded oligonucleotide and/or PCR amplification products.

Illustrative Computer Architecture

Figure 8:
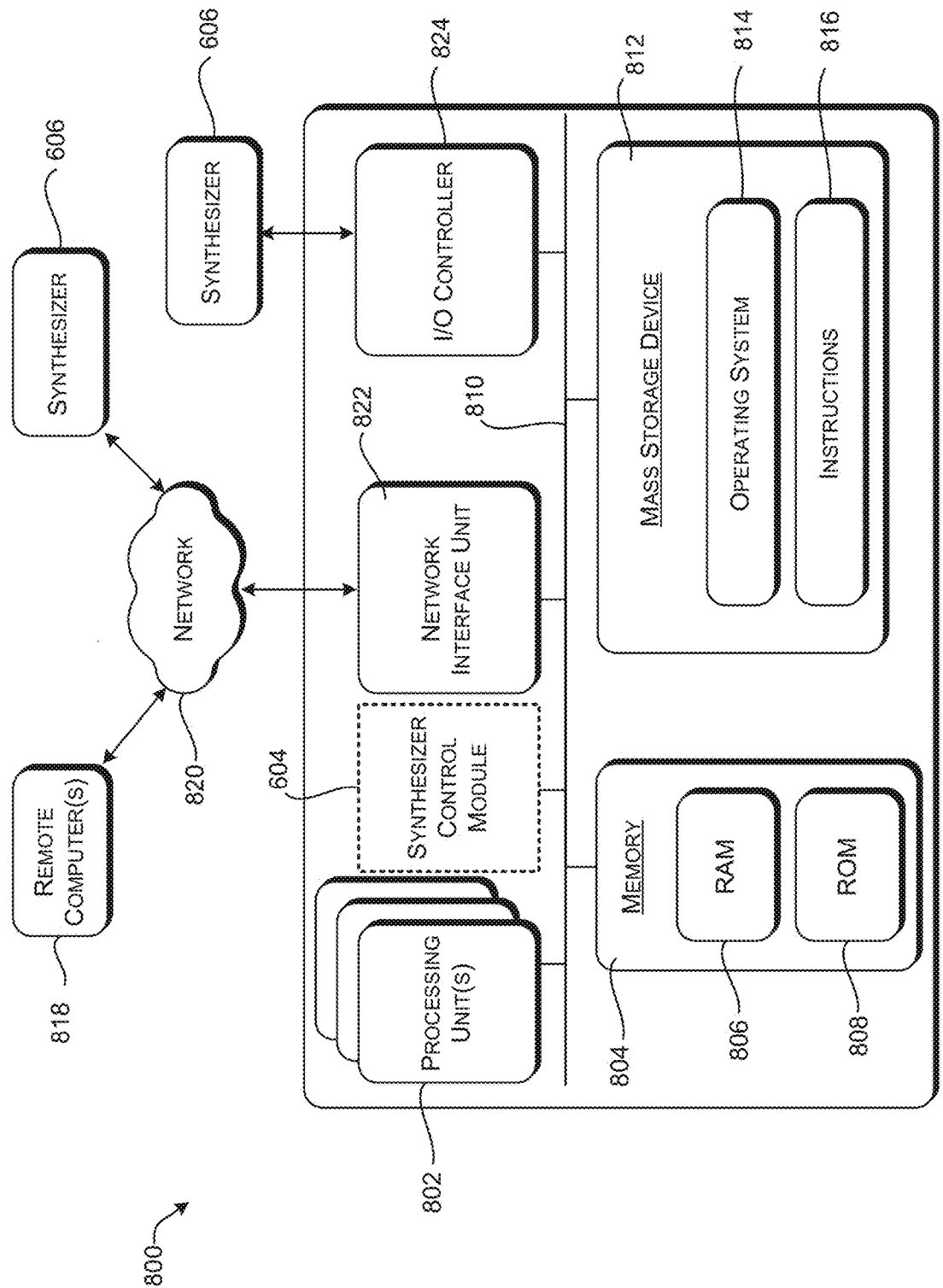
FIG. 8 is an illustrative computer architecture for implementing techniques of this disclosure.

FIG. 8 is a computer architecture diagram showing an illustrative computer hardware and software architecture for a computing device such as the computing device 602 introduced FIG. 6. In particular, the computer 800 illustrated in FIG. 8 can be utilized to implement the synthesizer control module 604.

The computer 800 includes one or more processing units 802, a system memory 804, including a random-access memory 806 ("RAM") and a read-only memory ("ROM") 808, and a system bus 810 that couples the memory 804 to the processing unit(s) 802. A basic input/output system ("BIOS" or "firmware") containing the basic routines that help to transfer information between elements within the computer 800, such as during startup, can be stored in the ROM 808. The computer 800 further includes a mass storage device 812 for storing an operating system 814 and other instructions 816 that represent application programs and/or other types of programs such as, for example, instructions to implement the synthesizer control module 604. The mass storage device 812 can also be configured to store files, documents, and data.

The mass storage device 812 is connected to the processing unit(s) 802 through a mass storage controller (not shown) connected to the bus 810. The mass storage device 812 and its associated computer-readable media provide non-volatile storage for the computer 800. Although the description of computer-readable media contained herein refers to a mass storage device, such as a hard disk, CD-ROM drive, DVD-ROM drive, or USB storage key, it should be appreciated by those skilled in the art that computer-readable media can be any available computer-readable storage media or communication media that can be accessed by the computer 800.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules or other data. For example, computer-readable storage media includes, but is not limited to, RAM 806, ROM 808, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 800. For purposes of the claims, the phrase "computer-readable storage medium," and variations thereof, does not include waves or signals per se or communication media.

According to various configurations, the computer 800 can operate in a networked environment using logical connections to a remote computer(s) 818 through a network 820. The computer 800 can connect to the network 820 through a network interface unit 822 connected to the bus 810. It should be appreciated that the network interface unit 822 can also be utilized to connect to other types of networks and remote computer systems. The computer 800 can also include an input/output controller 824 for receiving and processing input from a number of other devices, including a keyboard, mouse, touch input, an electronic stylus (not shown), or equipment such as a synthesizer 606 for synthesizing oligonucleotides. Similarly, the input/output controller 824 can provide output to a display screen or other type of output device (not shown).

It should be appreciated that the software components described herein, when loaded into the processing unit(s) 802 and executed, can transform the processing unit(s) 802 and the overall computer 800 from a general-purpose computing device into a special-purpose computing device customized to facilitate the functionality presented herein. The processing unit(s) 802 can be constructed from any number of transistors or other discrete circuit elements, which can individually or collectively assume any number of states. More specifically, the processing unit(s) 802 can operate as a finite-state machine, in response to executable instructions contained within the software modules disclosed herein. These computer-executable instructions can transform the processing unit(s) 802 by specifying how the processing unit(s) 802 transitions between states, thereby transforming the transistors or other discrete hardware elements constituting the processing unit(s) 802.

Encoding the software modules presented herein can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 800 to store and execute the software components presented herein. It also should be appreciated that the architecture shown in FIG. 8 for the computer 800, or a similar architecture, can be utilized to implement many types of computing devices such as desktop computers, notebook computers, servers, supercomputers, gaming devices, tablet computers, and other types of computing devices known to those skilled in the art. For example, the computer 800 may be wholly or partially integrated into the synthesizer 606. It is also contemplated that the computer 800 might not include all of the components shown in FIG. 8, can include other components that are not explicitly shown in FIG. 8, or can utilize an architecture completely different than that shown in FIG. 8.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of selectively assembling an oligonucleotide on a microelectrode array (102) coated with a plurality of anchor sequences (108), the method comprising: introducing a first oligonucleotide complex (110) encoding a first arbitrary value into a reaction chamber (610) containing the microelectrode array (102); activating a first subset of electrodes (104) in the microelectrode array (102) to attract the first oligonucleotide complex (110) to the first subset of electrodes (104) having attached thereto a first subset of anchor sequences (108); introducing a second oligonucleotide complex (112) encoding a second arbitrary value into the reaction chamber (610); activating a second subset of electrodes (104) in the microelectrode array (102) to attract the second oligonucleotide complex (110) to the second subset of electrodes (104) having attached thereto a second subset of anchor sequences (108); and closing nicks in assembled double-stranded oligonucleotides (402) attached to the microelectrode array (102), the assembled double-stranded oligonucleotides (402) formed at least in part by hybridization of the first oligonucleotide complex (110) to the first subset of anchor sequences (108) or by hybridization of the second oligonucleotide complex (112) to the second subset of anchor sequences (108).

Clause 2. The method of clause 1, wherein the first arbitrary value represents a first binary digit and the second arbitrary value represents a second binary digit.

Clause 3. The method of any of clauses 1-2, wherein closing the nicks comprises introducing a ligase into the reaction chamber.

Clause 4. The method of any of clauses 1-2, wherein an end of the first oligonucleotide complex is an azide and an end of the second oligonucleotide complex is an alkyne; and wherein, closing the nicks comprises initiating Cu(I)-catalyzed azide-alkyne cycloaddition (CuAAC).

Clause 5. The method of any of clauses 1-4, further comprising separating the assembled double-stranded oligonucleotides from the microelectrode array.

Clause 6. The method of any of clauses 1-5, wherein a sticky end of the first oligonucleotides complex has a sequence that hybridizes to any of the plurality of anchor sequences.

Clause 7. The method of any of clauses 1-6, further comprising: introducing a third oligonucleotide complex into the reaction chamber containing the microelectrode array, the third oligonucleotide complex having alternate sticky ends, wherein the third oligonucleotide complex is an alternate configuration of the first oligonucleotide complex or of the second oligonucleotide complex; and activating a third subset of electrodes in the microelectrode array to attract the third oligonucleotide complex to the third subset of electrodes, wherein the alternate sticky ends of the third oligonucleotide complex hybridize with sticky ends of the first oligonucleotide complex or with sticky ends of the second oligonucleotide complex.

Clause 8. A system for selectively assembling an oligonucleotide, the system (600) comprising: a microelectrode array (102) coated with a plurality of anchor sequences (108); a reaction chamber (610) in contact with the microelectrode array (102); a first fluid delivery pathway (614A-F) configured to introduce a first oligonucleotide complex (110) encoding a first arbitrary value into the reaction chamber (610); a second fluid delivery pathway (614A-F) configured to introduce a second oligonucleotide complex (112) encoding a second arbitrary value into the reaction chamber (610); and control circuitry (612) configured to selectively activate individual electrodes (104) in the microelectrode array (102), selectively open the first fluid delivery pathway (614A-F), and selectively open the second fluid delivery pathway (614A-F) in response to instructions (608) indicating a sequence of an assembled double-stranded oligonucleotide (402).

Clause 9. The system of clause 8, further comprising: a third fluid delivery pathway configured to deliver an alternate configuration of the first oligonucleotide complex having alternate sticky ends; and a fourth fluid delivery pathway configured to deliver an alternate configuration of the second oligonucleotide complex having alternate sticky ends.

Clause 10. The system of any of clauses 8-9, further comprising a third fluid delivery pathway configured to introduce a ligase into the reaction chamber.

Clause 11. The system of any of clauses 8-9, further comprising a third fluid delivery pathway configured to introduce a copper species into the reaction chamber.

Clause 12. The system of any of clauses 8-11, wherein the control circuitry is configured to, in response to instructions indicating completion of synthesis, introduce an enzyme that cleaves the assembled double-stranded oligonucleotide from the microelectrode array or introduce a chemical that cleaves a linker attaching the assembled double-stranded oligonucleotide to the microelectrode array.

Clause 13. The system of any of clauses 8-12, wherein the sequence of the assembled double-stranded oligonucleotide is provided in the instructions to the control circuitry as an ordered sequence of values including the first arbitrary value and the second arbitrary value.

Clause 14. The system of any of clauses 8-13, further comprising a fourth fluid delivery pathway configured to introduce the anchor sequences into the reaction chamber under conditions that cause the anchor sequences to coat the microelectrode array.

Clause 15. A method of encoding data by selectively assembling an oligonucleotide, the method comprising: attaching a plurality of anchor sequences (108) to a surface of a microelectrode array (102); hybridizing first initiating oligonucleotide complexes (214) encoding a first arbitrary value with a subset of the plurality of anchor sequences (108) attached to a subset of electrodes (104) in the microelectrode array (102) by activating the subset of electrodes (104) and introducing the first initiating oligonucleotide complexes (214) into a solution contacting the surface of the microelectrode array (102); hybridizing second oligonucleotide complexes (112A) encoding a second arbitrary value with the first initiating oligonucleotide complexes (214) by activating the subset of electrodes (104) and introducing the second oligonucleotide complexes (112A) into the solution contacting the surface of the microelectrode array (102); hybridizing alternate configurations of the second oligonucleotide complexes (112B) encoding the second arbitrary value with the second oligonucleotide complexes (112A) by activating the subset of electrodes (104) and introducing the alternate configurations of the second oligonucleotide complexes (112B) into the solution contacting the surface of the microelectrode array (102); closing nicks in assembled double-stranded oligonucleotides (402) formed from the hybridizing of the anchor sequences (108), the first initiating oligonucleotide complexes (214), the second oligonucleotides complexes (112A), and the alternate configurations of the second oligonucleotides complexes (112B); and separating the assembled double-stranded oligonucleotides (402) from the surface of the microelectrode array (102).

Clause 16. The method of clause 15, wherein the first initiating oligonucleotide complexes are partially double-stranded oligonucleotides comprising a long sticky end that hybridizes to at least a portion of the anchor sequences and a second sticky end that hybridizes to other oligonucleotide complexes.

Clause 17. The method of clause 16, wherein the second oligonucleotide complexes are partially double-stranded oligonucleotides comprising a first sticky end that hybridizes to the second sticky end of the first initiating oligonucleotide complexes and a second sticky end that hybridizes to other oligonucleotide complexes.

Clause 18. The method of clause 17, wherein the alternate configurations of the second oligonucleotide complexes are partially double-stranded oligonucleotides comprising a first sticky end that hybridizes to the second sticky end of the second oligonucleotide complexes and a second sticky end that hybridizes to the first sticky end of the second oligonucleotide complexes.

Clause 19. The method of any of clauses 15-18, further comprising hybridizing first oligonucleotide complexes (110) encoding the first arbitrary value with the alternate configurations of the second oligonucleotide complexes (112B) by activating a subset of electrodes (104) introducing the first oligonucleotide complexes (110) into the solution contacting the surface of the microelectrode array (102).

Clause 20. The method of any of clauses 15-18, further comprising decoding the data by sequencing one or both strands of the assembled double-stranded oligonucleotides.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method of selectively assembling an oligonucleotide on a microelectrode array coated with a plurality of anchor sequences, the method comprising:
   introducing a first oligonucleotide complex encoding a first arbitrary value into a reaction chamber containing the microelectrode array;
   activating a first subset of electrodes in the microelectrode array to attract the first oligonucleotide complex to the first subset of electrodes having attached thereto a first subset of anchor sequences;
   introducing a second oligonucleotide complex encoding a second arbitrary value into the reaction chamber;
   activating a second subset of electrodes in the microelectrode array to attract the second oligonucleotide complex to the second subset of electrodes having attached thereto a second subset of anchor sequences; and
   closing nicks in assembled double-stranded oligonucleotides attached to the microelectrode array, the assembled double-stranded oligonucleotides formed at least in part by hybridization of the first oligonucleotide complex to the first subset of anchor sequences or by hybridization of the second oligonucleotide complex to the second subset of anchor sequences.

2. The method of claim 1, wherein the first arbitrary value represents a first binary digit and the second arbitrary value represents a second binary digit.

3. The method of claim 1, wherein closing the nicks comprises introducing a ligase into the reaction chamber.

4. The method of claim 1, wherein an end of the first oligonucleotide complex is an azide and an end of the second oligonucleotide complex is an alkyne; and
   wherein, closing the nicks comprises initiating Cu(I)-catalyzed azide-alkyne cycloaddition (CuAAC).

5. The method of claim 1, further comprising separating the assembled double-stranded oligonucleotides from the microelectrode array.

6. The method of claim 1, wherein a sticky end of the first oligonucleotide complex has a sequence that hybridizes to any of the plurality of anchor sequences.

7. The method of claim 1, further comprising:
   introducing a third oligonucleotide complex into the reaction chamber containing the microelectrode array, the third oligonucleotide complex having alternate sticky ends, wherein the third oligonucleotide complex is an alternate configuration of the first oligonucleotide complex or of the second oligonucleotide complex; and
   activating a third subset of electrodes in the microelectrode array to attract the third oligonucleotide complex to the third subset of electrodes, wherein the alternate sticky ends of the third oligonucleotide complex hybridize with sticky ends of the first oligonucleotide complex or with sticky ends of the second oligonucleotide complex.

8. The system of claim 1, further comprising:
   means for introducing a third oligonucleotide complex into the reaction chamber containing the microelectrode array, the third oligonucleotide complex having alternate sticky ends, wherein the third oligonucleotide complex is an alternate configuration of the first oligonucleotide complex or of the second oligonucleotide complex; and
   means for activating a third subset of electrodes in the microelectrode array to attract the third oligonucleotide complex to the third subset of electrodes, wherein the alternate sticky ends of the third oligonucleotide complex hybridize with sticky ends of the first oligonucleotide complex or with sticky ends of the second oligonucleotide complex.

9. A system for selectively assembling an oligonucleotide, the system comprising:
   a microelectrode array coated with a plurality of anchor sequences;
   a reaction chamber containing the microelectrode array;
   means for introducing a first oligonucleotide complex encoding a first arbitrary value into the reaction chamber;
   means for activating a first subset of electrodes in the microelectrode array to attract the first oligonucleotide complex to the first subset of electrodes having attached thereto a first subset of anchor sequences;
   means for introducing a second oligonucleotide complex encoding a second arbitrary value into the reaction chamber;
   means for activating a second subset of electrodes in the microelectrode array to attract the second oligonucleotide complex to the second subset of electrodes having attached thereto a second subset of anchor sequences; and
   means for closing nicks in assembled double-stranded oligonucleotides attached to the microelectrode array, the assembled double-stranded oligonucleotides formed at least in part by hybridization of the first oligonucleotide complex to the first subset of anchor sequences or by hybridization of the second oligonucleotide complex to the second subset of anchor sequences.

10. The system of claim 9, wherein the first arbitrary value represents a first binary digit and the second arbitrary value represents a second binary digit.

11. The system of claim 9, wherein the means for closing the nicks comprises a ligase introduced into the reaction chamber.

12. The system of claim 9, wherein an end of the first oligonucleotide complex is an azide and an end of the second oligonucleotide complex is an alkyne; and
   wherein, the means for closing the nicks comprises initiation of Cu(I)-catalyzed azide-alkyne cycloaddition (CuAAC).

13. The system of claim 9, further comprising means for separating the assembled double-stranded oligonucleotides from the microelectrode array.

14. The system of claim 9, wherein a sticky end of the first oligonucleotide complex has a sequence that hybridizes to any of the plurality of anchor sequences.

15. A system for selectively assembling an oligonucleotide, the system comprising:
   a microelectrode array coated with a plurality of anchor sequences;
   a reaction chamber containing the microelectrode array;
   a first fluid delivery pathway configured to introduce a first oligonucleotide complex encoding a first arbitrary value into the reaction chamber;
   control circuitry configured to selectively activate a first subset of electrodes in the microelectrode array to attract the first oligonucleotide complex to the first subset of electrodes having attached thereto a first subset of anchor sequences;
   a second fluid delivery pathway configured to introduce a second oligonucleotide complex encoding a second arbitrary value into the reaction chamber;

the control circuitry further configured to selectively activate a second subset of electrodes in the microelectrode array to attract the second oligonucleotide complex to the second subset of electrodes having attached thereto a second subset of anchor sequences; and a third fluid delivery pathway configured to introduce a reagent to close nicks in assembled double-stranded oligonucleotides attached to the microelectrode array, the assembled double-stranded oligonucleotides formed at least in part by hybridization of the first oligonucleotide complex to the first subset of anchor sequences or by hybridization of the second oligonucleotide complex to the second subset of anchor sequences.

16. The system of claim 15, wherein the first arbitrary value represents a first binary digit and the second arbitrary value represents a second binary digit.

17. The system of claim 15, wherein the reagent to close the nicks comprises a ligase.

18. The system of claim 15, wherein an end of the first oligonucleotide complex is an azide and an end of the second oligonucleotide complex is an alkyne; and wherein, the reagent to close the nicks comprises a copper species that initiates Cu(I)-catalyzed azide-alkyne cycloaddition (CuAAC).

19. The system of claim 15, wherein the control circuitry further configured to introduce an enzyme that cleaves the assembled double-stranded oligonucleotide from the microelectrode array or introduce a chemical that cleaves a linker attaching the assembled double-stranded oligonucleotide to the microelectrode array thereby separating the assembled double-stranded oligonucleotides from the microelectrode array.

20. The system of claim 15, wherein a sticky end of the first oligonucleotide complex has a sequence that hybridizes to any of the plurality of anchor sequences.

* * * * *